United States Patent
Miller et al.

(10) Patent No.: US 10,383,996 B2
(45) Date of Patent: Aug. 20, 2019

(54) INJECTION DEVICE WITH A PROCESSOR FOR COLLECTING EJECTION INFORMATION

(75) Inventors: Thomas Miller, Bronshoj (DK); Christian Peter Enggaard, Vejby (DK); Preben Nielsen, Holbæk (DK); Bodo von Münchow, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 104 days.

(21) Appl. No.: 11/665,623

(22) PCT Filed: Oct. 20, 2005

(86) PCT No.: PCT/EP2005/011284
§ 371 (c)(1),
(2), (4) Date: Feb. 4, 2008

(87) PCT Pub. No.: WO2006/045525
PCT Pub. Date: May 4, 2006

(65) Prior Publication Data
US 2008/0188813 A1    Aug. 7, 2008

Related U.S. Application Data

(60) Provisional application No. 60/626,514, filed on Nov. 10, 2004.

(30) Foreign Application Priority Data

Oct. 21, 2004    (EP) .................................... 04077898

(51) Int. Cl.
*A61M 5/20*    (2006.01)
*A61M 5/24*    (2006.01)
(Continued)

(52) U.S. Cl.
CPC .... *A61M 5/14566* (2013.01); *A61M 5/31525* (2013.01); *A61M 5/3202* (2013.01);
(Continued)

(58) Field of Classification Search
CPC ................ A61M 5/24; A61M 2205/50; A61M 5/31525; A61M 5/31546; A61M 5/31553;
(Continued)

(56) References Cited

U.S. PATENT DOCUMENTS 2,807,012 A    9/1957 Schwarz
4,321,461 A    3/1982 Walter, Jr. et al.
(Continued)

FOREIGN PATENT DOCUMENTS

DE    29904864    8/2000
DE    10116361    10/2002
(Continued)

OTHER PUBLICATIONS

Non-Final Office Action dated May 13, 2011 in U.S. Appl. No. 11/665,572, filed Apr. 17, 2007 by Enggaard et al.
(Continued)

*Primary Examiner* — Lauren P Farrar
(74) *Attorney, Agent, or Firm* — Leon Y. Lum

(57) ABSTRACT

A medication delivery device comprises an injection device having a reservoir comprising a medicament to be ejected, and a sensor arranged to detect an ejection of the medicament from the injection device, the sensor being arranged to output a signal comprising ejecting information, and a processor for collecting and storing the ejection information.

11 Claims, 14 Drawing Sheets

(51) Int. Cl.

| | | |
|---|---|---|
| *A61M 5/31* | (2006.01) | |
| *A61M 5/32* | (2006.01) | |
| *A61M 5/145* | (2006.01) | |
| *A61M 5/315* | (2006.01) | |
| *G01D 21/00* | (2006.01) | |
| *G01D 5/245* | (2006.01) | |
| *G01F 11/02* | (2006.01) | |

(52) U.S. Cl.
CPC ........... *G01D 5/2451* (2013.01); *G01D 21/00* (2013.01); *G01F 11/029* (2013.01); *A61M 5/20* (2013.01); *A61M 5/24* (2013.01); *A61M 5/31553* (2013.01); *A61M 2005/3125* (2013.01); *A61M 2005/3126* (2013.01); *A61M 2205/3317* (2013.01); *A61M 2205/3389* (2013.01); *A61M 2205/50* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2209/086* (2013.01)

(58) Field of Classification Search
CPC .......... A61M 5/31585; A61M 5/16831; A61M 5/172; A61M 5/3155; A61M 2205/3576; A61M 2205/6018; A61M 5/14566; A61M 5/3202; A61M 2205/3317; A61M 2209/086; A61M 2205/3389; A61M 2005/3125; A61M 2005/3126; A61M 5/20; A61M 2205/587; A61M 2205/52; A61M 2205/582; A61M 2205/583; A61M 2205/581; G01D 5/2451; G01D 21/00; G01F 11/029
USPC .......... 604/65, 118, 121, 187, 189, 192–198, 604/207, 246, 260; 705/3
See application file for complete search history.

(56) References Cited

U.S. PATENT DOCUMENTS

| | | | |
|---|---|---|---|
| 4,498,904 A | 2/1985 | Turner et al. | |
| 4,515,584 A | 5/1985 | Abe et al. | |
| 4,592,745 A | 6/1986 | Rex et al. | |
| 4,634,431 A | 1/1987 | Whitney et al. | |
| 4,636,201 A | 1/1987 | Ambrose et al. | |
| 4,812,724 A | 3/1989 | Langer et al. | |
| 4,838,860 A | 6/1989 | Groshong et al. | |
| 4,869,722 A | 9/1989 | Heyman | |
| 4,883,472 A | 11/1989 | Michel | |
| 4,898,578 A | 2/1990 | Rubalcaba | |
| 4,959,056 A | 9/1990 | Dombrowski et al. | |
| 4,973,318 A | 11/1990 | Holm et al. | |
| 4,985,015 A | 1/1991 | Obermann et al. | |
| 5,002,536 A | 3/1991 | Thompson et al. | |
| 5,009,640 A | 4/1991 | Pyret et al. | |
| 5,017,190 A | 5/1991 | Simon et al. | |
| 5,098,400 A | 3/1992 | Crouse et al. | |
| 5,125,268 A | 6/1992 | Caron | |
| 5,221,268 A | 6/1993 | Barton et al. | |
| 5,254,102 A | 10/1993 | Ogawa | |
| 5,272,917 A | 12/1993 | Pippert | |
| 5,279,586 A | 1/1994 | Balkwill | |
| 5,295,965 A * | 3/1994 | Wilmot ............... A61M 5/2033 604/136 |
| 5,363,842 A | 11/1994 | Mishelevich et al. | |
| 5,494,036 A | 2/1996 | Uber et al. | |
| 5,509,905 A | 4/1996 | Michel | |
| 5,522,799 A | 6/1996 | Furukawa | |
| 5,536,249 A | 7/1996 | Castellano et al. | |
| 5,573,506 A | 11/1996 | Vasko | |
| 5,582,598 A | 12/1996 | Chanoch | |
| 5,593,390 A | 1/1997 | Castellano et al. | |
| 5,662,612 A | 9/1997 | Niehoff | |
| 5,690,618 A | 11/1997 | Smith et al. | |
| 5,704,922 A | 1/1998 | Brown | |
| 5,725,508 A | 3/1998 | Chanoch et al. | |
| 5,728,074 A * | 3/1998 | Castellano et al. ........... 604/207 |
| 5,782,814 A | 7/1998 | Brown et al. | |
| 5,795,333 A | 8/1998 | Reilly et al. | |
| 5,807,336 A | 9/1998 | Russo et al. | |
| 5,843,047 A | 12/1998 | Pyrozyk et al. | |
| 5,855,839 A | 1/1999 | Brunel | |
| 5,873,856 A | 2/1999 | Hjertman et al. | |
| 5,920,198 A | 7/1999 | Suzuki et al. | |
| 5,928,197 A | 7/1999 | Niehoff | |
| 5,947,934 A | 9/1999 | Hansen et al. | |
| 5,998,989 A | 12/1999 | Lohberg | |
| 6,019,745 A | 2/2000 | Gray | |
| 6,113,578 A | 9/2000 | Brown | |
| 6,235,004 B1 | 5/2001 | Steenfeldt-Jensen et al. | |
| 6,268,722 B1 | 7/2001 | Kogure et al. | |
| 6,277,099 B1 * | 8/2001 | Strowe et al. ................. 604/207 |
| 6,287,283 B1 | 9/2001 | Ljunggreen et al. | |
| 6,482,185 B1 | 11/2002 | Hartmann | |
| 6,514,230 B1 | 2/2003 | Munk et al. | |
| 6,547,755 B1 | 4/2003 | Lippe et al. | |
| 7,025,743 B2 | 4/2006 | Mann et al. | |
| 7,138,806 B2 * | 11/2006 | Gafner ............... A61M 5/31556 324/660 |
| 7,144,384 B2 | 12/2006 | Gorman et al. | |
| 7,161,488 B2 | 1/2007 | Frasch | |
| 7,195,616 B2 | 3/2007 | Diller et al. | |
| 8,221,356 B2 | 7/2012 | Enggaard et al. | |
| 2002/0029018 A1 * | 3/2002 | Jeffrey ........................ 604/209 |
| 2002/0188419 A1 * | 12/2002 | Slate ...................... A61M 5/20 702/176 |
| 2003/0055685 A1 | 3/2003 | Cobb et al. | |
| 2004/0074652 A1 | 4/2004 | Ginell | |
| 2004/0171983 A1 | 9/2004 | Sparks et al. | |
| 2004/0207385 A1 | 10/2004 | Gafner et al. | |
| 2004/0210199 A1 * | 10/2004 | Atterbury ......... A61M 5/31535 604/224 |
| 2005/0020969 A1 * | 1/2005 | Slate et al. ...................... 604/65 |
| 2005/0041531 A1 | 2/2005 | Sekura | |
| 2005/0182360 A1 | 8/2005 | Yeandel et al. | |
| 2006/0047538 A1 | 3/2006 | Condurso et al. | |
| 2006/0135907 A1 | 6/2006 | Remde et al. | |
| 2008/0140018 A1 | 6/2008 | Enggaard et al. | |
| 2008/0188813 A1 | 8/2008 | Miller et al. | |
| 2008/0312604 A1 | 12/2008 | Boesen | |
| 2009/0069742 A1 | 3/2009 | Larsen | |

FOREIGN PATENT DOCUMENTS

| | | |
|---|---|---|
| DE | 10201875 | 5/2003 |
| DK | PA 2001 00240 | 11/2001 |
| EP | 327910 A2 | 8/1989 |
| EP | 387854 | 9/1990 |
| EP | 568321 A2 | 11/1993 |
| EP | 635277 | 1/1995 |
| EP | 1074273 | 2/2001 |
| EP | 1095668 | 5/2001 |
| EP | 1321158 A1 | 6/2003 |
| EP | 1361908 | 11/2003 |
| EP | 1393764 | 3/2004 |
| EP | 04077898.7 | 10/2004 |
| EP | 1804868 | 5/2006 |
| EP | 1726322 | 11/2006 |
| FR | 2740345 | 4/1997 |
| JP | H10-89910 | 4/1998 |
| JP | 10-504729 | 5/1998 |
| JP | 2002531154 A | 9/2002 |
| JP | 2003-310758 | 11/2003 |
| JP | 2006507856 A | 3/2006 |
| RU | 2080882 | 6/1997 |
| SU | 1760462 | 9/1992 |
| WO | WO 90/09202 | 8/1990 |
| WO | 90/10470 | 9/1990 |
| WO | WO 95/24233 | 9/1995 |
| WO | WO9524233 | 9/1995 |
| WO | WO 97/30742 | 8/1997 |

(56) References Cited

FOREIGN PATENT DOCUMENTS

| WO | WO 97/304742 | 8/1997 |
|----|----|----|
| WO | WO 97/33638 | 9/1997 |
| WO | WO 99/15214 | 4/1999 |
| WO | WO 01/26710 | 4/2001 |
| WO | WO 02/43573 | 6/2002 |
| WO | 02064196 | 8/2002 |
| WO | WO02064196 | 8/2002 |
| WO | 02092153 | 11/2002 |
| WO | WO 02/092153 | 11/2002 |
| WO | WO 03/005891 | 1/2003 |
| WO | WO 03/009461 | 1/2003 |
| WO | WO 03/047426 | 6/2003 |
| WO | WO 03/103753 | 12/2003 |
| WO | 2004030717 A2 | 4/2004 |
| WO | WO 04/030717 | 4/2004 |
| WO | WO 2004/098390 | 11/2004 |
| WO | WO 2004/110528 | 12/2004 |
| WO | 2005005929 A2 | 1/2005 |
| WO | WO 05/042076 | 5/2005 |
| WO | WO2006045525 | 5/2006 |
| WO | 2006087712 A2 | 8/2006 |

OTHER PUBLICATIONS

English Abstract of JP2003-310758 Published Nov. 5, 2003.
Tränkler, 1996, "Taschenbuch Der Messtechnik," R. Oldenbourg Verlag München Wien pp. 181, 190.
International Search Report from PCT/EP2007/052636, dated Jul. 30, 2007.
International Search Report from PCT/EP2005/011282, Filed Oct. 20, 2005.
DE 29904864 English Abstract, published Aug. 3, 2000.
DE 10201875 English Abstract, published May 22, 2003.
DE 10116361 English Abstract, published Oct. 10, 2002.
FR 2740345 English Abstract, published Oct. 26, 1995.
Final Office Action dated May 14, 2009 in U.S. Appl. No. 11/665,572, filed Feb. 4, 2008 by Enggaard et al.
Non-Final Office Action dated Sep. 19, 2008 in U.S. Appl. No. 11/665,572, filed Feb. 4, 2008 by Enggaard et al.
Notice of Allowance dated Aug. 31, 2005 in U.S. Appl. No. 10/076,025, filed Feb. 13, 2002 by Larsen et al.
Non-Final Office Action dated Nov. 28, 2003 in U.S. Appl. No. 10/076,025, filed Feb. 13, 2002 by Larsen et al.
Excerpts from The Compact Edition of the Oxford English Dictionary Complete Text Reproduced Micrographically, copyright Oxford University press 1971, re-issued 1987, pp. 366 and 367.
Webpage printout from www.merriam-webster.com. entry Integral.
Hard copy of Sanofi Aventis website, retrieved on Jul. 23, 2015.
Hard copy of Timesulin TM website, retrieved on Jul. 23, 2015.
Certified priority document, EP04077898.7, filed Oct. 21, 2004, Applicant Novo Nordisk AS.
Wikipedia. "Camera Phone." https://en.wikipedia.org/wiki/Camera_phone#directory. Updated Dec. 19, 2015. Accessed Dec. 23, 2015.
Excerpt from "Providing Diabetes Care in General Practice" Table 11.8 Published 2007 by Class Publishing, London.
Package scan of NovoLog (R) FlexPen (R) as a "prefilled" device; scanned Aug. 17, 2015.

* cited by examiner

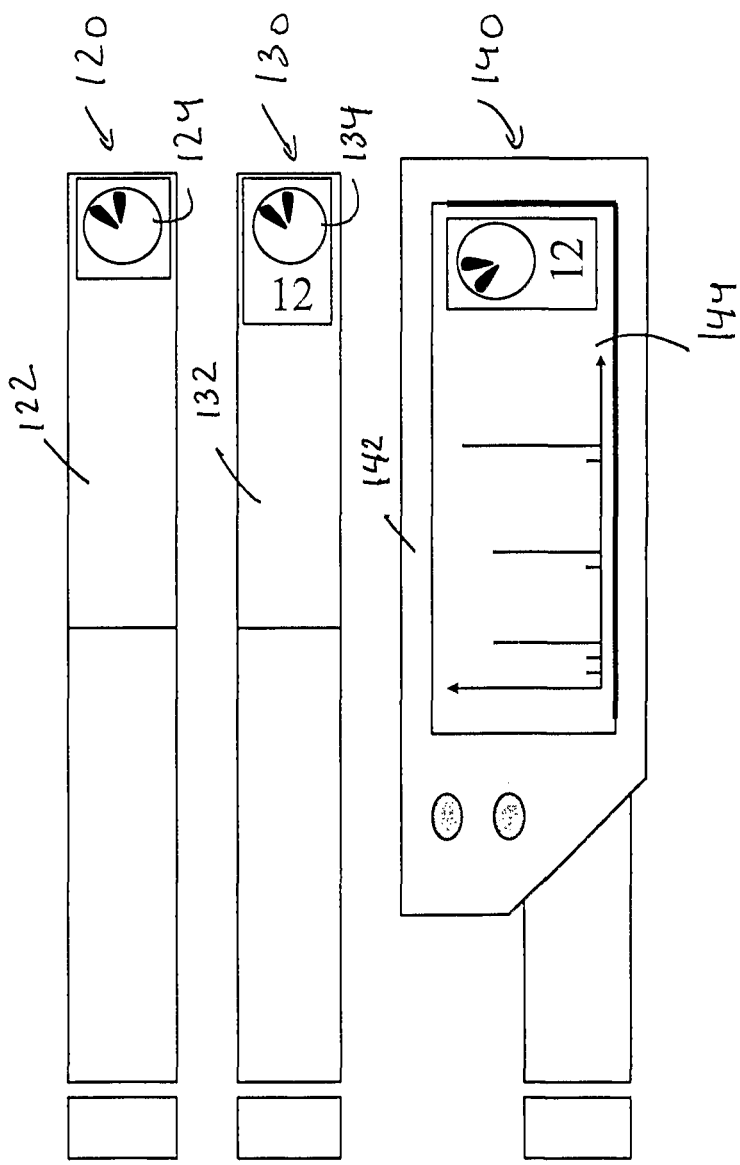

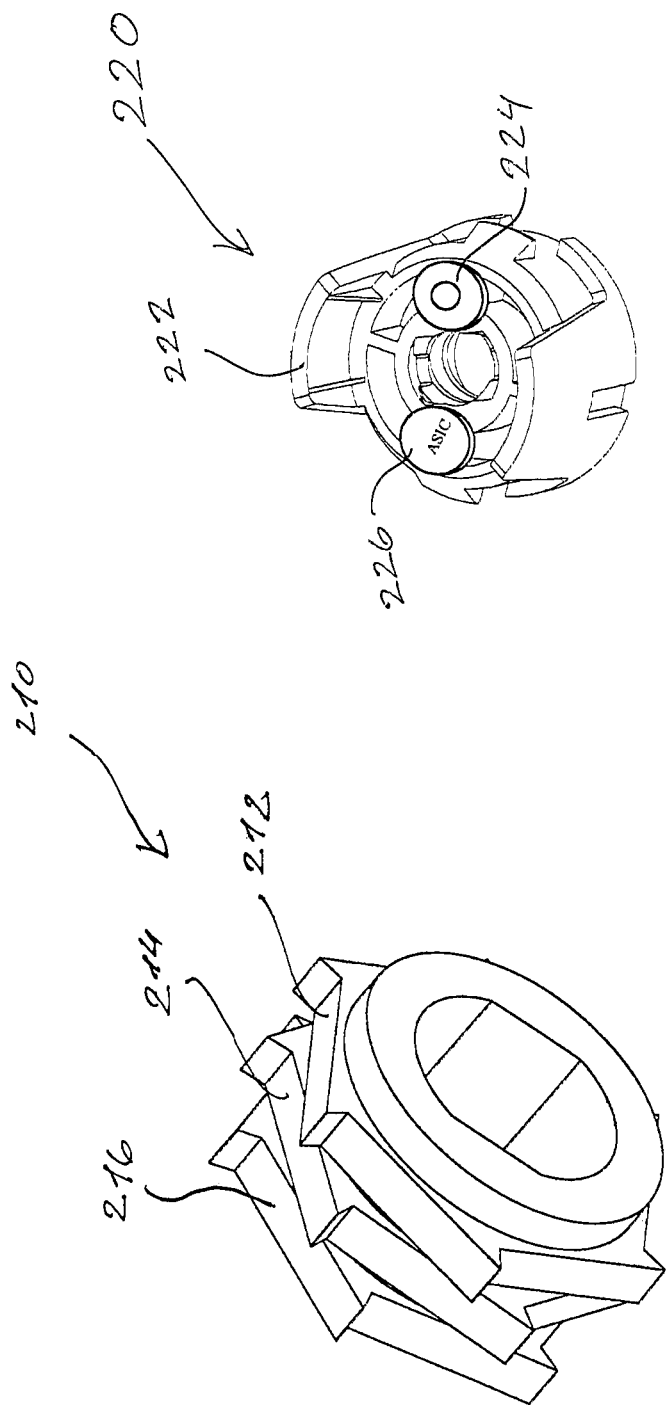

INJECTION DEVICE WITH A PROCESSOR FOR COLLECTING EJECTION INFORMATION

CROSS-REFERENCE TO RELATED APPLICATIONS

This application is a 35 U.S.C. § 371 national stage application of International Patent Application PCT/EP2005/011284 (published as WO 2006/045525), filed Oct. 20, 2005, which claimed priority of European Patent Application 04077898.7, filed Oct. 21, 2004; this application further claims priority under 35 U.S.C. § 119 of U.S. Provisional Application 60/626,514, filed Nov. 10, 2004.

FIELD OF THE INVENTION

The present invention relates to an injection device adapted to record ejection information, such as information related to time elapsed since the last injection or dose quantity of an injected medicament. In particular the present invention relates to a medication delivery device comprising an injection device, a sensor arranged to output a signal comprising ejection information and an processor for collecting and storing the ejection information.

BACKGROUND OF THE INVENTION

Performing the necessary insulin injection at the right time and in the right size is essential for managing diabetes, i.e. compliance with the specified insulin regimen is important. In order to make it possible for medical personnel to determine the effectiveness of a prescribed dosage pattern, diabetes patients are encouraged to keep a log of the size and time of each injection. However, such logs are normally kept in handwritten notebooks, from the logged information may not be easily uploaded to a computer for data processing. Furthermore, as only events, which are noted by the patient, are logged, the note book system requires that the patient remembers to log each injection, if the logged information is to have any value in the treatment of the patient's disease. A missing or erroneous record in the log results in a misleading picture of the injection history and thus a misleading basis for the medical personnel's decision making with respect to future medication. Accordingly, it may be desirable not only to automate the logging of ejection information from medication delivery systems, but also to provide a foolproof system.

Devices which log the time and size of the last injected doses are known in the art. One such device is known from WO 97/30742, which discloses a syringe having an electric representation of parameters such as magnitude of the set dose and the latest injected dose, which syringe further has a stop watch, the status of which is electronically represented and is together with electronic represented parameters reproduced in a display showing the number of hours passed since the last operation.

It is an object of a preferred embodiment of the present invention to provide a medication delivery device which comprises as few and as inexpensive components as possible, while at the same time being able to log the use pattern of the device and ejected information.

Furthermore it is an object of a preferred embodiment of the present invention to provide a solution, wherein patient security is high, such that a wrong drug is not inserted into the injection device by accident and such that dose log information of one type of medication is not mistaken for another.

BRIEF SUMMARY OF THE INVENTION

In a first aspect, the invention provides a medication delivery device comprising an injection device having a reservoir comprising a medicament to be ejected, the device further comprising:
  a sensor arranged to detect an ejection of the medicament from the injection device, the sensor being arranged to output a signal comprising ejecting information, and
  a processor for collecting and storing the ejection information.

The reservoir may form an integral part of the device, whereby the user is prohibited from inserting a wrong medicament into the device. Such a wrong medicament could be a different type than intended or the intended medicament in a wrong concentration. One disadvantage of injecting a wrong medicament could be that the log is misleading, resulting in mistreatment. Another and more serious disadvantage is that injection of a wrong drug could have lethal consequences. When the reservoir forms an integral part of the device the device may be a medication delivery pen.

It will thus be appreciated that the present device may be regarded as a pre-filled device, i.e. a device in which it is not possible to exchange the drug reservoir. In addition to the improved patient security offered by such a device, it is a further advantage of a pre-filled device over a refillable one that good dexterity is often required in order to exchange the drug compartment or ampoule. Thus, the device of the present invention offers an attractive alternative to persons with poor dexterity.

In embodiments wherein the injection device defines a reservoir forming an integral part of the device, the device may be regarded as a disposable device. Accordingly, it may be desirable from a manufacturing point of view that the electronic components are as few and as inexpensive as possible. For example, in preferred embodiments of the invention, no electronic display is provided in the device.

Alternatively, the device may be durable such that the reservoir may be changed a plurality of times during the life time of the device.

One or more sensors may be provided in order to collect ejection information. The sensor(s) may for example determine movement of a piston or of piston rod of the device and/or that a force is applied to a part, e.g. an end part, of the piston or piston rod and/or an absolute or relative position of the piston and/or the pressure in the reservoir as a function of time.

An example of a simple sensor is one that only outputs ejection information which is not per se readable or understandable by a patient or by medical personnel, but which must be translated or converted in order for it to be understandable. Such a simple signal could be the displacement of the piston in a length unit, e.g. microns, or a rotation angle, which must be converted into a volume unit, e.g. ml, or a unit indicating an amount of the useful drug, e.g. mmol or IU, in order to be understandable. Such a conversion can be performed by the processor. Alternatively, the sensor may be adapted to transform the ejection information into a format which is understandable to the user. Thus, the sensor may comprise a data processing unit performing the conversion.

The sensor is adapted to output a signal comprising ejection information. Additionally, other parts of the device may be able to provide ejection information e.g. ejection information relating to the type of the medicament in the reservoir.

In the context of the present invention, the term 'sensor' shall be understood as a device that responds to a physical stimulus, such as thermal energy, electromagnetic energy, acoustic energy, pressure, magnetism, or motion, by producing a signal, e.g. electrical.

In the context of the present invention the term "injection device" shall be understood as an instrument for introducing fluids into or withdrawing them from the body. The terms "syringe device" and "medication delivery device" may be used as synonyms for an injection device in the context of the present invention.

Also in the context of the present invention, the term 'output' shall be understood so as to cover both embodiments wherein the sensor comprises a power supply and thus on its own is capable of sending a sensor signal and embodiments wherein a first signal must be send into the sensor so as to provide a second signal. An example of the latter, is a sensor which changes resistance in response to rotation and thus a first electrical signal must be send into the sensor in order to provide a second return signal.

Furthermore, in the context of the present invention, there is distinguished between 'ejection' and 'injection'. By 'ejection' is meant that a dose of the drug is ejected out of the syringe, but not necessarily injected into the body of the patient, whereas 'injection' means that a dosage of the drug is ejected out of the syringe and into the body of a patient.

It should be understood that the term 'processor' in the sense of the present invention may include electronic means capable of receiving and storing information.

It is a common problem that air bobbles may be trapped inside the reservoir at the stage of producing a drug reservoir. In case of intra vascular injections, the air bubbles are undesired, as they may block capillary veins, e.g. in the brain. If the injections are performed subcutaneous or intra muscular, the air will be perceived as annoying or painful for the patient, as the injected volume is larger than necessary. Accordingly, it may be desirable to allow an ejection to be performed without a needle of the device being inserted into the body of the patient in order to expel air from the reservoir. This however, provides the problem of providing a log which shows actual injections and not all ejections, some of which have not been performed as injections. Thus, the device may make it possible to perform non-logged ejections or to erase some of the ejection information e.g. the last performed ejection. In some embodiments the erroneous information is not deleted in connection whit the ejection but is removed by a computer into which the ejection information is loaded. This may as an example be done at the physician.

In one embodiment the medication delivery device further comprises a communication means e.g. electronic, arranged to transmit the ejecting information to an external data receiving device. The data receiving device may be a personal computer or a portable device. The communication makes it possible to analyse the ejection information at an external device e.g. a computer at the premises of a physician. Furthermore, the communication means allows monitoring and possibly processing of the ejection information at an external device, such that the injection device only needs to include such equipment which is necessary in order to record the ejection information. Accordingly, the device may be manufactured more inexpensively than if the device were to include means for e.g. processing and displaying ejection information.

The external data receiving device may form an integral part of a cover for covering at least a needle portion of the injection device. The cover may comprise at least one of: a display device for displaying a representation of the ejecting information, and a storage device for storing a representation of the ejecting information.

In one embodiment, the processor of the device is only able to store one set of ejection information, e.g. the time of the last ejection and the size of the dose. Thus, in order to provide a log containing information from more than one ejection, the cover or another data receiving device may be attached to the device, so that the information may be transferred to the storage device of the cover. Possibly, the processor of the device may be reset once the information has been transferred to the storage device of the cover, so that the device is ready to record ejection information of a subsequent ejection. Alternatively, the information in the processor may be overwritten, when the subsequent ejection if performed. An advantage of the embodiments incorporating a storage device in the cover is that the processor in the device may be minimised, as the requirements to the storage capabilities are limited.

In another embodiment, the processor of the device is able to store a number of sets of ejection information, e.g. enough to store the all the ejections performed during the use period of the reservoir, such as 100 sets or 50 sets of ejection information. However, it may still be advantageous to include a storage device in the cover, as such a storage device makes it possible to collect ejection information from more than one device. If the cover is adapted to collect information from more than one device, it may be desirable that the ejection information communicated to the cover comprises information about the device, such as the type of medicament contained in the device and/or an identification insignia identifying the device. Especially, when the user uses more than one type of medicament or different concentrations of the same medicament, e.g. so-called "long acting" and "fast acting" insulin.

The display of the cover may be adapted to display more than one type of information at the same time, e.g. the time since the last ejection and the size of the dose. Alternatively, the display may be adapted to display only one type of information at the time, in which case there may be provided user-operable means allowing a user to switch between the different types of information displayed, such user-operable means comprising e.g. a push button. The cover may be adapted to display information automatically, when the cover is attached to the device, or when data is transferred from the device to the cover. Such information may comprise the information which is being, or has just been, transmitted, or a calculation performed on the basis of the information just transmitted. It can be possible for the user to configure the cover to display specific information, when the device is inserted into the cover, or to configure the cover to display a specific sequence of information.

As it will be appreciated from the above description, the provision of a simple device with an interface makes it possible to produce a plurality of covers which may serve the needs of different patients, and which may be adapted to meet a variety of different medication logging requirements. As an example, it will be possible to provide covers, each comprising a display and a data processor such that different kinds of ejection information may be presented in a plurality of different ways. Alternatively, simple covers comprising a simple data processor and a simple LED may be provided.

The ejection information may comprise time of at least one ejected dose, the time being e.g. recorded in hours, minutes or seconds. The time may be relative to the last ejection and/or the actual time of the last ejection. Furthermore, the time of each ejection and/or the size of each ejection may be comprised in the ejection information. The identification of the injection device and/or the identification of the type of medicament may also be a part of the ejection information. The device may be programmable, e.g. at the premises of a physician, so as to designate a specific device to a specific user, such that the ejection information comprises identification of the user, an identification of the physician or medical centre ordering the medicament, and a schedule for the injection of the drug. This minimizes the risk of the device being used by another patient. Furthermore, the ejection information may comprise information concerning an expiry date of the medicament comprised in the device.

It may be desirable that the device is adapted to communicate with more than one device, e.g. the cover and a cradle connected to a computer. Accordingly, the communication means can comprise one single interface arranged to communicate data to the external data receiving device, e.g. the cover, and to communicate data to a further external data receiving device, e.g. the cradle. The single interface may be arranged such that the device is only able to communicate with one device at the time, e.g. either the cover or the cradle.

In one embodiment, the cover is also provided with an interface, such that the device may simultaneously communicate with the cover, and such that the cover may communicate with a further device, e.g. a personal computer. In this embodiment, an inexpensive interface may be provided between the injection device and the cover, whereas a more expensive interface may be provided in the cover. Thus, it is possible to minimise the production costs of the device and still provide the advantages of a more expensive interface, e.g. wireless or optical, as it is located in the reusable cover.

In another embodiment, the single interface is adapted to communicate with two devices at the same time, whereby a communication protocol controls the communication with the two devices. As an example, the device can be adapted to communicate with both the cover and a personal computer at the same time.

Alternatively, the communication means may comprise two separate interfaces, one of which is arranged to communicate data to the external data receiving device of the cover, and another one of which is arranged to communicate data to a further external data receiving device.

The cover and/or communication means of the device may comprise at least one of: an electrical conductor, a device for wireless data transmission, a device for optical data transmission, a device for acoustical data transmission and a device for inductive data transmission.

If two separate interfaces are provided, one of them may comprise electrical conductors and the other may be wireless. As an example, the interface between the cover and the device may be constituted by electrical conductors which interengage when the cover and the device are attached to each other, whereas a wireless interface may be provided for communication to a personal computer. The wireless interface may be based on infrared technology or RF-technology, such as IrDA, RFid, Bluetooth, DECT etc. The outer surface of the device may be provided with electrical conductors which are adapted to engage electrical conductors provided on the inner surface of the cover.

In one embodiment, the cover is attachable to the injection device, such that an ejection may only be performed when the cover is removed from the injection device. The cover may comprise a cap adapted to be realisably attached to the device. In one embodiment, the device comprises an processor for collecting and storing the ejection information, and a display in the cover. In the latter embodiment, an ejection may only be performed when the cover is removed and, thus when the display is separated from the device.

The sensor of the medication delivery device may for example incorporate
- a movable part adapted to move relative to a stationary part during ejection of a dose of a medicament from the system and/or during setting of a dose to be ejected; and
- at least two conductors which are arranged such that an electrical characteristic is defined by the mutual position of the movable and the stationary part and/or by movement of one of said parts relative to the other;
- a detector for detecting a change of said electrical characteristic, so as to provide a signal indicative of the amount of the ejected dose or of the set dose.

The movable part may be movable by translation or by rotation. The stationary part may co-axially encapsulate the movable part e.g. such that both co-extend in an axial direction of the device and such that the movable part is provided inside the stationary part. A housing of the injection device may define the stationary part. In other embodiments the stationary part is attached to the housing of the device.

The movable part may be connected to a piston rod of the device. Translational movement of the piston rod may cause a part of the medicament of be ejected from the injection device.

The piston rod may have a threaded outer surface and a part of the device may be adapted to receive the piston rod as it has a corresponding threaded inner surface. In the latter embodiment rotational movement of the piston rod may also result in a translational movement of the piston rod.

In one embodiment the movable part and the stationary part is able to rotate more then one revolution i.e. more than 360 degrees, during setting of the dose or during ejection. In such embodiments the medical device may comprise a counter which is able to count the number of revolutions performed.

There may be provided at least two conductors between which the detector may be provided. Alternatively, the detector may be connected to the electrical conductors of the device. As an example a resistance between the conductors changes depending on the relative position of the movable part and the stationary part and thus the detector may be a device adapted to detect resistance between two elements.

In embodiments wherein the movable part is adapted to rotate relative to the stationary part during ejection of a set dose of a medicament, the detector may be used to determine the ejected dose such that the user may keep a log of the ejection history and the ejection times.

In embodiments wherein the movable part is adapted to rotate relative to the stationary part during setting of a dose, there may be provided a sensor which is able to determine when an ejection starts and/or when it is finished. Thus, the ejected dose may be calculated using information about the set dose at the time of starting the ejection and the remaining dose when finishing the ejection. In the latter embodiment detector may be a detector capable of determining translational movement e.g. of the piston rod, but not necessarily the length of the travelled distance.

In case the movable part is movable by translation, such as linear translation, the movable part may e.g. constitute a portion of the piston rod, or it may constitute a part which is integral with the piston rod.

The electrical characteristic may be one of an electrical inductance, a capacitance, an electric resistance, a voltage and an electrical current. The electrical inductance may e.g. be impedance or capacitance. In the latter case the electrical conductors may be connected to surfaces of conductive material which are spaced apart from each other. The relative position of the two surfaces determines the capacitance. In one embodiment the surfaces are provided as two half circles which may be rotated between two positions a first position wherein they overlap each other entirely and a second position wherein the do not overlap at all. In an alternative to the latter embodiment one of the surfaces moves translationally while rotating, whereby the distance between the surfaces changes. Thus, when the movable part has rotated one revolution the capacity between the plates has changed as the distance between the plates has changes. Thus, it is possible to determine both the relative angular position of the surfaces and the number of revolutions which have been performed.

In yet another embodiment a coil may be provided between the two conductors. The coil may be provided on stationary part. At the same time a magnetic material may be provided on the movable part and thus movement of the movable part induces a current between the two conductors. In the latter embodiment the relative movement of the stationary part and the movable part may be determined.

From the above it may be appreciated that the electrical characteristic between the two conductors may depend on relative position and or on relative movement of the movable part and the stationary part.

The movable part may comprise a first electrically conducting surface, and the stationary part may comprise a second electrically conducting surface, the electrical characteristic of the at least two electrical conductors being determined by relative movement and/or relative position of said first and second surfaces. In one embodiment there is provided two conductors a first which is electrically connected to the first electrically conducting surface and a second conductor which is electrically connected to the second electrically conducting surface.

A primary set of contact surfaces may be arranged to engage and disengage upon relative movement of the stationary part and the movable part, the primary set of contact surfaces may comprise a first and a second contact surface which comprises the first and the second electrical surfaces, respectively.

In a preferred embodiment the first conductor is connected to the first conducting surface which is provided on the first contact surface and the second conductor is connected to the second conducting surface which is provided on the second contact surface.

In one embodiment a secondary set of contact surfaces may be arranged to engage and disengage upon relative movement of the stationary part and the movable part, the secondary set of contact surfaces may comprise a third and a fourth contact surface which may comprise a third and a fourth electrical surface, respectively. Furthermore, the electrical characteristic between the primary set of contact surfaces may be unchanged when the electrical characteristic between the secondary set of contact surfaces is changed and vice versa. Thus, at no time two or more electrical characteristic are changed at the same time.

In one embodiment the rotatable part comprises both the first and the third electrically conducting surfaces which are provided on the same contact surfaces.

Biasing arms may be provided which are biased towards the periphery of the movable part, said arms comprising at least one of the second and the fourth conducting surfaces. In one embodiment there is provided two biasing arms one defining the second conducting surface and one defining the fourth conducting surface.

The outer periphery of the movable part may define a plurality of conductive and non-conductive surfaces which may define the first and the third contact surfaces.

A visible and/or audible and/or tactile indication may detectable when the second or the fourth contact surface changes from a conductive to a non-conductive surface. Accordingly, the system changes status electronically, the user may be able to identify a change e.g. as he hears or feels a 'click'.

The periphery of the movable part, may comprise abrupt changes in the radial dimension. Such abrupt changes may be used to ensure that the movable part is only able of rotating in one direction. The changes may also be used to provide a tactile or audible indication which may be generated by rotating the movable part such that an biased arm changes position from a point with a large radial dimension to a point with a small radial dimension, where by a 'click' may be generated.

The contact surfaces may arranged to lock for relative rotational movement in one direction. The lock may be provided by the abrupt change in the radial dimension.

A processor may be provided to collect the information detected from the detector. Such a processor may be an electronic processor comprising a memory. In one embodiment the arrangement comprises a power supply and an ASIC connected to the at least two conductors. The ASIC may be adapted to collect the information from the detector and to transform the information into a format known to the user. As an example the collected information is in one embodiment degrees of rotation of the movable part relative to the stationary part. In the embodiment rotation of a piston rod results in rotation of the movable part and as the outer surface of the piston rod is threaded, rotation of the piston rod results in a translational movement of the piston rod such that volume of the medicament is ejected. Accordingly, the ASIC of said embodiment may transform the degrees of rotation into a distance in the axial direction which again may be transformed into the volume of the medicament which is ejected.

In a second aspect, the present invention provides to an injection device for a medication delivery device according to any of the preceding claims, the injection device comprising:
  a sensor arranged to detect an ejection of a medicament from the injection device;
  an processor for collecting ejection information detected by the sensor;
  communication means for transmitting ejection information to said data receiving device of said cover.

The injection device may be adapted to be inserted into a medication delivery device such that it forms an integral part of the medication delivery device when it arrives at the consumer. The above discussion of the features of the device of the first aspect of the invention also apply to the injection device of the second aspect.

In a third aspect, the present invention provides a cover for a medication delivery device according to the first aspect of the invention, comprising an data receiving device and signal receiving means for receiving said ejecting information, the cover further comprising at least one of:
  a storage device for storing the ejection information and
  a display device for displaying the ejection information.

The cover may comprise any feature or element described in relation to the cover described in connection with the first aspect of the invention. Especially the cover may comprise an interface adapted to communicate with a corresponding interface of a medication delivery device such that data may be transferred between the cover and the device.

A plurality of different covers may be provided, each cover being designed to meet different needs. As an example, one type of cover only comprises an LED adapted to emit ejection information, while another type of cover comprises a display which may display different types of ejection at the same time. Furthermore, the covers may be provided in different designs and materials to result in a variety of different aesthetic appearances.

Finally, the invention provides a kit comprising a medication delivery device according to to the first aspect of the invention, and a cradle comprising means for performing at least one of:
supplying electrical power to the data receiving device of the cover;
transmitting data between the medication delivery device and an external computer.

The cradle may be adapted to be connected to a computer, e.g. by a wired or a wireless connection. The cradle may be used to synchronise data between the device and a program being executed by the computer, e.g. such that a physician may analyse the data and alter the drug delivery schedule or programme.

Furthermore, the cradle may be used to transfer power to the device. One advantage of such a solution is that a battery possibly included in the device may be minimised, as it may be recharged. The Cradle may be connected to more than one computer. The cradle may be in the form of a cover for protecting the device.

DETAILED DESCRIPTION OF THE INVENTION

The invention will now be described in further detail with reference to the drawings, in which:

FIGS. 4-6 show three different embodiments of a cover for a medication delivery device;

FIGS. 10-21 illustrate various parts of a sensor arrangement for detecting a quantity of a dose of drug ejected from an embodiment of medication delivery pen, the movable part of which is rotational;

Figure 1:
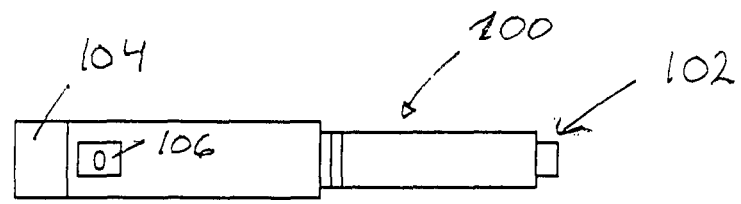
FIGS. 1 and 2 show a medication delivery device in the form of a pen and a cover therefor.
Figure 2:
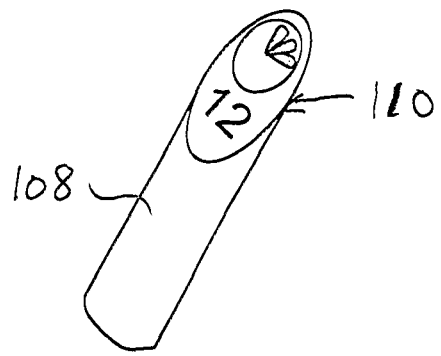
Figure 3:
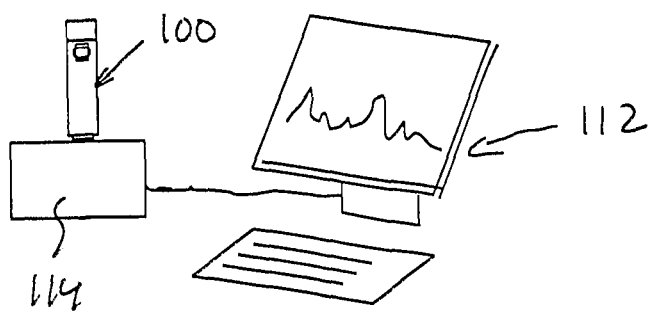
FIG. 3 shows the pen of FIG. 1 connected to an external computer via a cradle.

The medication delivery device in the form of a pen 100 of FIG. 1 comprises a needle portion 102 comprising a needle for insertion into a patient's body (the needle is not shown in FIG. 1). At its proximal end the pen body is provided with a knob 104 which can be rotated by an operator, e.g. the patient, to set a dose of drug to be ejected from the pen, the drug being contained in the pen. The set dose is indicated in a display window 106. Further details of the pen will be understood from the below description of FIG. 7. The pen cover (or "cap") 108 of FIG. 2 comprises a display 110 for displaying e.g. a dose quantity of an ejected dose and the time elapsed since that dose was ejected from the pen. For example, the number 12 in the display may indicate that the last ejected dose was 12 IU, and the three shadowed areas in the display may indicate that at least three hours have elapsed since that dose was ejected. In FIG. 3, the pen 100 is connected to an external data receiving device in the form of a personal computer 112 via a cradle 114. The computer 112 is adequately programmed to load, store and display information transmitted by the electronic components of the pen, cf. the below description of FIG. 8. For example, the computer 112 may be programmed to graphically display the ejected doses of the drug as a function of time in a bar diagram.

FIGS. 4-6 show three different medication delivery devices 120, 130 and 140, each comprising a cover 122, 132 and 142 with a display portion 124, 134, 144. The display portion 124 of device 120 comprises means for displaying one information only, e.g. time elapsed since last ejection, whereas the display portion 134 of device 130 is arranged to display two information items, e.g. time elapsed since last ejection and quantity of last ejected dose. Finally, display portion 142 of device 140 is arranged to display three different information items, e.g. in addition to those discussed above also a illustration of a plurality of past ejection doses in a bar diagram.

Figure 7:
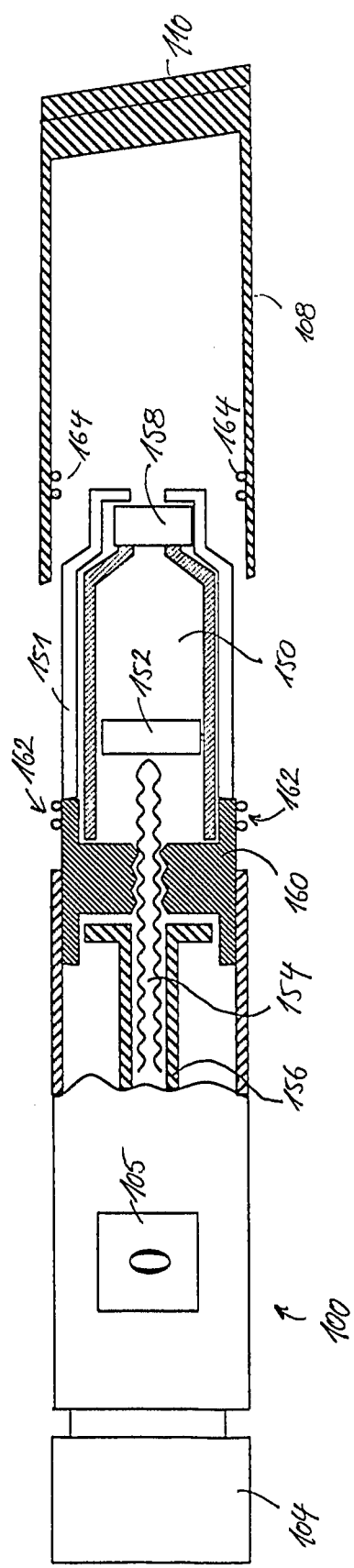
FIG. 7 is a schematic cross-sectional illustration of a medication delivery pen and a cover therefor.

The schematic cross-sectional view of pen 100 in FIG. 7 discloses various features of the pen. Though these features are described with reference to the pen 100, it should be understood that the same features may be equally provided in the pens 120, 130 and 140 of FIGS. 4-6. The pen 100 in FIG. 7 includes a drug cartridge or container 150, in which a piston 152 is arranged, so that it may slide in a distal direction (to the right in FIG. 7) under the action of a piston rod 154. The cartridge is secured in relation to the remaining parts of the pen by a cartridge holder 151. The piston rod 154 has a threaded outer surface which is guided in a ratchet 156. When drug ejection is activated by an operator, the ratchet and/or piston rod is influenced to cause the piston rod to move the piston 152 in the distal direction to force the drug out of the cartridge 150 through a needle (not shown) which extends through septum 158. Evidently, the cover 108 is removed prior to ejection of the dose. The pen further includes a nut 160 with an integrated sensor arrangement for detecting the size of an ejected dose, the sensor arrangement being further described below in connection with FIGS. 9-18. Electrical switches 162 provide an interface to external devices, such as to the cradle 114 of FIG. 3, or to the pen cover 108 which includes corresponding switches 164. The cover 108 may include a battery (not shown) for powering its display portion 110. The battery may conveniently be comprised in the distal end portion of the cover. A rotational dose setting member 104 may be used to set a dose, the set dose being e.g. indicated in a window 105. In general, the rotational movement of the piston rod 154 during ejection of the drug may be achieved as described in U.S. Pat. No. 6,235,004 which is hereby incorporated by reference.

Figure 8:
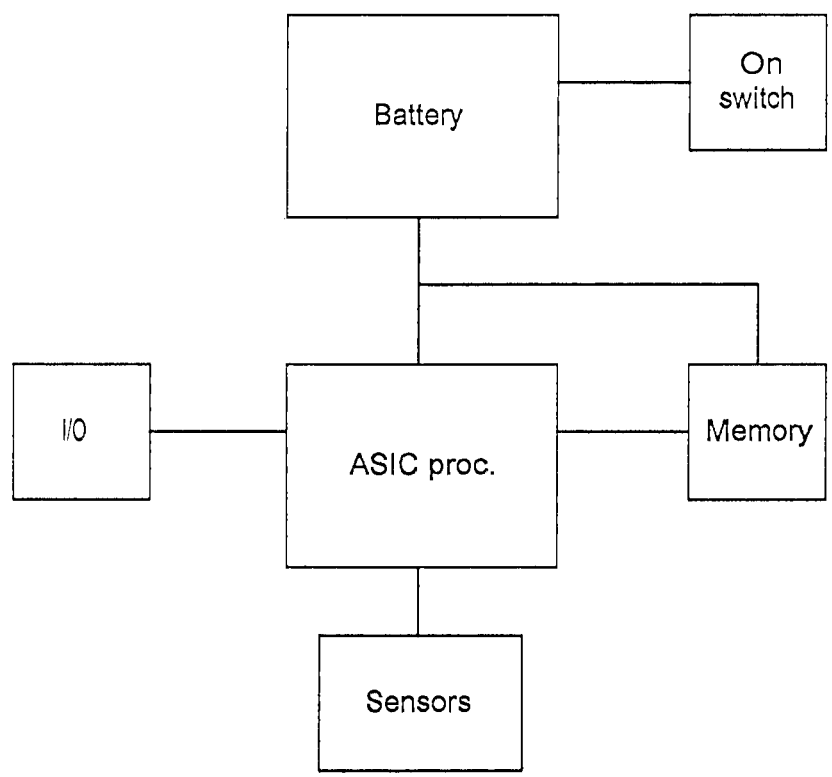
FIG. 8 is a schematic illustration of electronic components of an embodiment of a medication delivery device.
Figure 9:
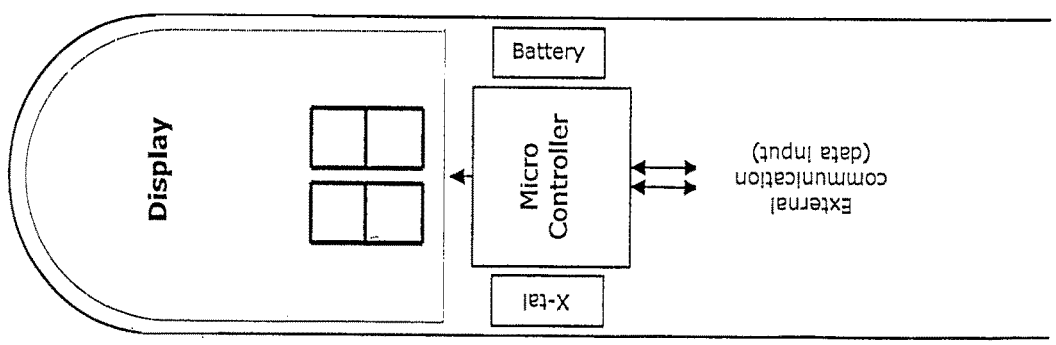
FIG. 9 is a schematic illustration of electronic components of an embodiment of a cover for a medication delivery pen.

FIG. 8 is a schematic illustration of electronic components of an embodiment of a medication delivery device. There is provided an "On switch" for allowing the battery to deliver power to an ASIC processor and to a memory connected to the ASIC processor. The processor is further connected an I/O device for communicating data via the switches 162 (cf. FIG. 7), and to one or more sensors, e.g. a sensor arrangement for detecting ejection information. In operation, the sensors may detect the quantity of an ejected dose which is communicated to the ASIC processor. The processor stores the quantity and the time of the ejection in the memory. Once the pen 100 is placed in the cradle 114 or once the cover 108 is placed over the needle portion of the pen, the ASIC processor initiates transfer of the information stored in the memory or a part of that information via the I/O device. The I/O device may also be used to clear the memory, such clearing being e.g. caused by an operator of the personal computer 112. The electronic components incorporated in the pen cover or cap 108 are illustrated in FIG. 9. A crystal (X-tal) serves as a clock generator for the microcontroller, which is powered by a battery, and which communicates with the electronic components of the pen via the external communication (data input) and with the display as illustrated.

Figure 10:
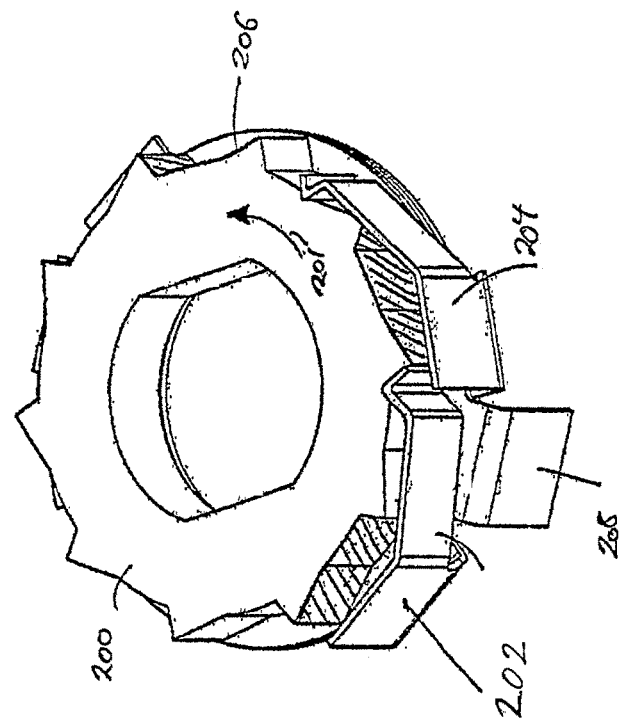

The nut 160 may for example constitute a part of the sensor arrangement of FIG. 10. The sensor arrangement comprises a first conductor in the form of a movable part 200 arranged to rotate in the direction of arrow 201 in relation to one or more second conductors in the form of stationary parts, e.g. arms 202 and 204, which are biased toward a peripheral edge 206 of the movable part 200. The hatched sections of the periphery 206 are non-conductive surface portions, whereas the non-hatched sections are conductive surface portions, i.e. first and third contact surfaces. Those end portions of the arms 202 and 204 which engage the periphery 206 define second and fourth contact surfaces. It will thus be appreciated that one of the arms via its engagement with the peripheral surface portion 206 defines a primary set of contact surfaces, while the other one of the arms via its engagement with the peripheral surface portion 206 defines a secondary set of contact surfaces. A conductive element 208 is provided for applying a voltage to the movable part 200. As illustrated, the periphery 206 defines abrupt changes of its radial dimension. These abrupt changes are also abrupt changes between conductive and non-conductive surface portions. Accordingly, as the movable part 200 is rotated relative to the arms 202 and 204, each of the arms will be charged in an alternating manner in accordance with its engagement with a conductive, i.e. charged, surface portion, or with a non-conductive, i.e. non-charged, surface portion. The changes in the two arms' respective charges can be recorded or detected, so that each voltage change in either one of the arms indicates a rotational increment of the movable part. This increment may indicate an incremental increase or decrease of a set dose, and/or an incremental increase of an ejected dose. Thanks to the abrupt changes in radial dimension of the movable part 200 and corresponding abrupt changes in surface conductivity, there is provided a mechanical coupling between the changes of the electrical characteristic and the rotation of the movable part. Accordingly, it is ensured that no increment is erroneously recorded without the movable part having actually been rotated.

FIG. 11 illustrates a different embodiment of a movable part 210 for determining an ejected and/or set dose. The peripheral surface of the part 210 comprises three sections 212, 214 and 216, each of which defines a plurality of abrupt changes of radial dimension and conductivity according to the same general principle as described above in connection with FIG. 10. The abrupt changes of each of the three sections are arranged with mutual angular displacements in order to decrease the detectable increments of a set or ejected dose portion which.

The sensor assembly 220 depicted in FIG. 12 includes the movable part 200 of FIG. 10 or the movable part 210 of FIG. 11 integrated with a support member 222 for mounting the sensor assembly in a housing of a medication delivery device. The support member 222 also supports a battery 224 and a processor 226, such as an ASIC processor.

Figure 13:
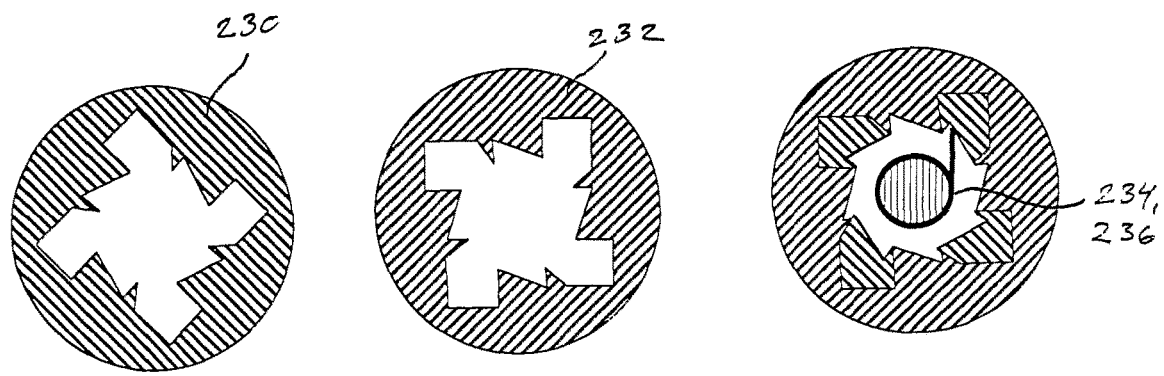
Figure 14:
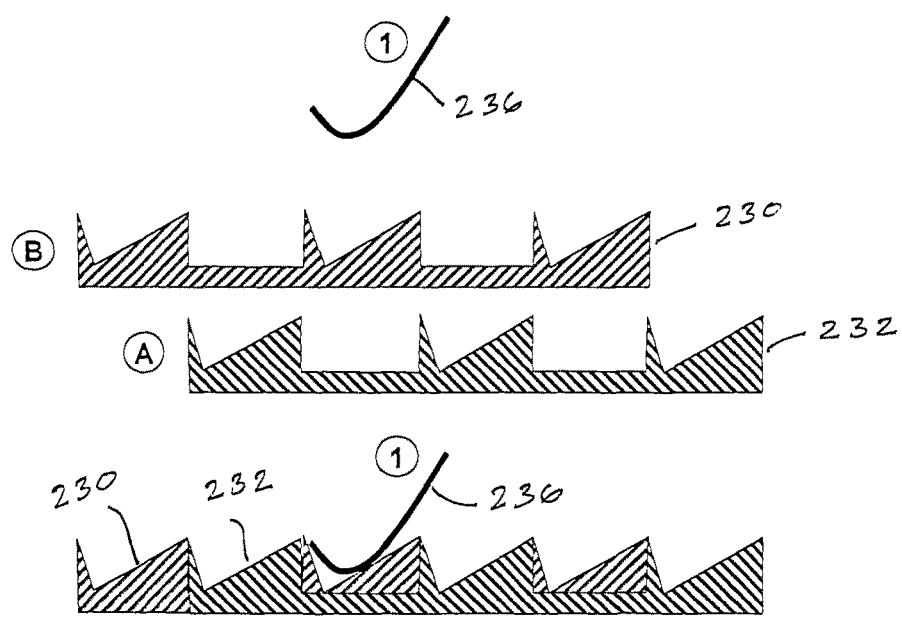
Figure 16:
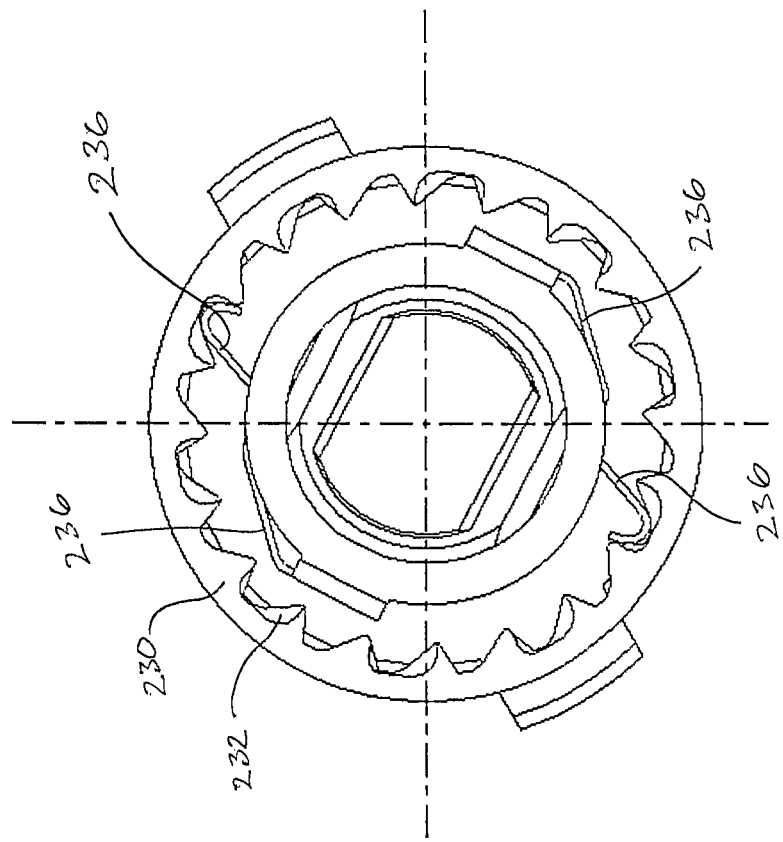
Figure 15:
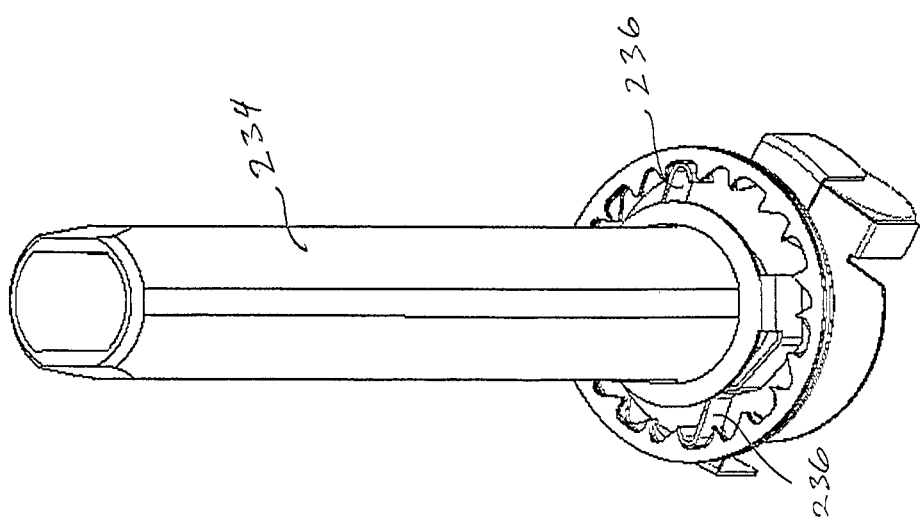

The embodiment of FIGS. 13-16 comprises two identical discs 230 and 232 arranged one above the other with a mutual angular displacement as illustrated in the far right drawing of FIG. 13. A core member 234 is arranged centrally within the discs, the core member carrying a ratchet arm 236 for engagement with one or the other disc. The discs are charged differently and arranged in electrical isolation from one another, so that the ratchet arm will produce a voltage output which varies as the ratchet arm 236 makes contact with one or the other disc 230, 232, cf. the illustrative view in the lower drawing of FIG. 14. As shown in FIGS. 15 and 16, there may be provided two arms 236. The core member may, cf. FIG. 15, extend out of the plane of the discs, so that rotation thereof may be effected by rotation of e.g. a dose setting member and/or a dose ejecting means (not shown in FIG. 15) connected to or integrated with the core member 234.

Figure 17:
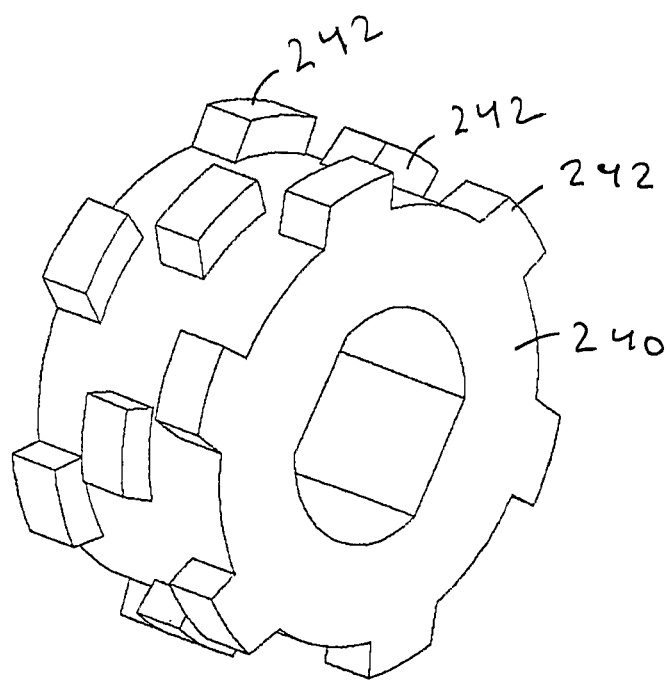
Figure 18:
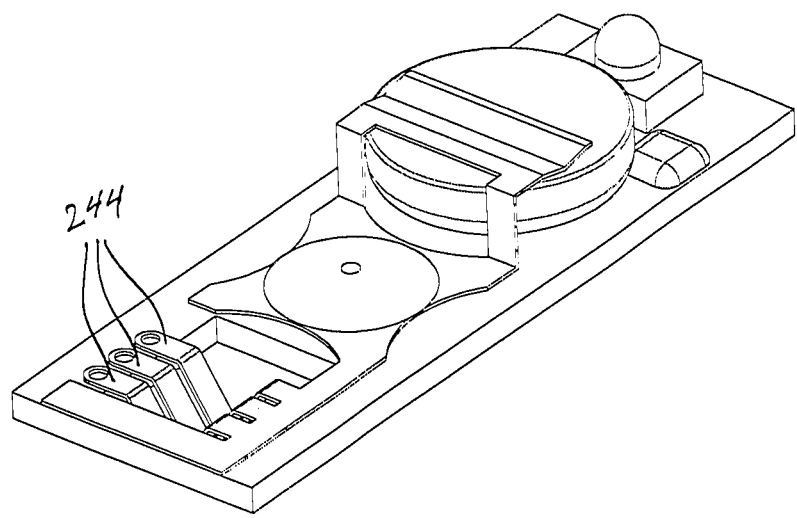

FIG. 17 shows a yet further embodiment of a movable part 240 which comprises three rows of protrusions 242 along its periphery. For example, the peripheral surfaces of the protrusions may be conductive, whereas the remaining peripheral surface of the movable part 240 may be non-conductive. The part 240 forms part of a sensor arrangement which also comprises an electronic circuit board as illustrated in FIG. 18, which comprises three arms 244 for engaging and disengaging the protrusions 242 to detect rotation of the movable part 240.

Figure 19:
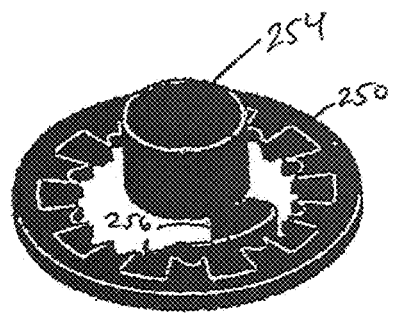

The sensor arrangement of FIG. 19 is similar to the arrangement of FIGS. 13-16 and comprises two discs at different voltages which are electrically insulated from one another. A core member 254 with a ratchet arm 256 makes alternating contact with one or the other disc to result in an alternating voltage output indicative of an increment or decrease of a set or an ejected dose of drug.

In the above embodiments, the electrical characteristic is described as a voltage. It should, however, be understood that the characteristic may also be any other detectable electrical property, such as a frequency of an alternating current.

Figure 20:
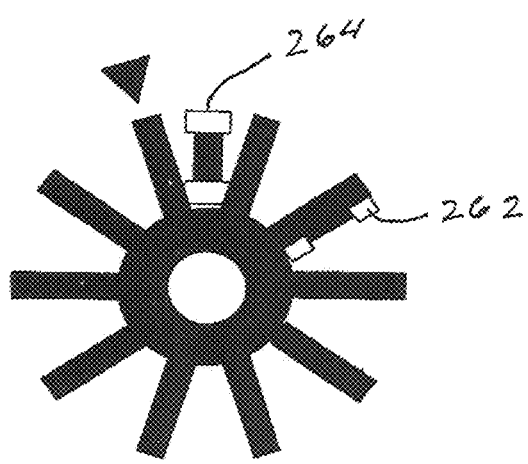

FIG. 20 illustrates an inductive sensor, in which a movable part is provided in the form of an anchor to inductors 262, 264. Induction can be measured or detected by an oscillating circuit, in which frequency changes are determined, or in which the rise time of the current in the inductor can be measured.

Figure 21:
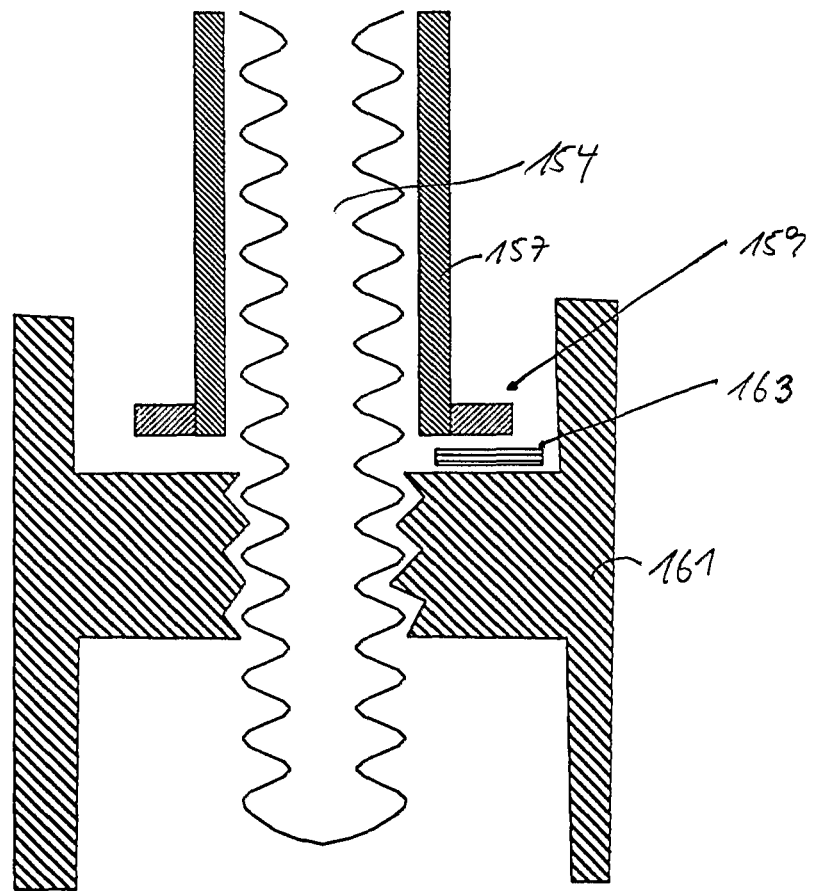

The embodiment of FIG. 21 also relies on an inductive principle, in which piston rod 154 is guided in a nut 161, the piston rod being enclosed by a conductive member 157, an end flange 159 of which is arranged in the vicinity of a coil 163.

Figure 22:
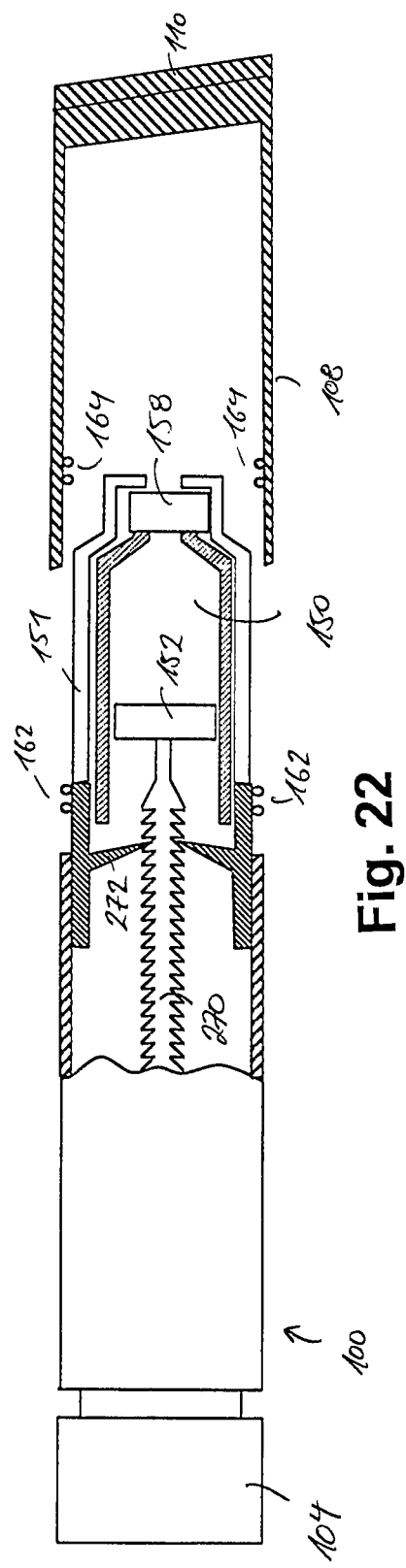
FIGS. 22-24 illustrate embodiments, the movable part of which is movable by translation.
Figure 24:
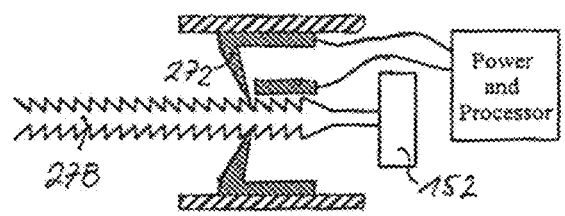
Figure 23:
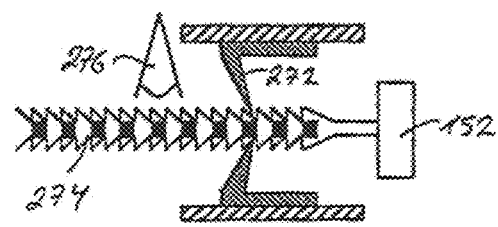

FIGS. 22-24 illustrate embodiments, the movable part of which is movable by translation.

In FIGS. 22-24, the characteristic may, as previously discussed, also be any other detectable electrical property, such as a frequency of an alternating current. To the extent that alike parts are included in the embodiment of FIGS. 22-24 as in the embodiment of FIGS. 1-21, the same reference numerals are used. Piston rod 270 has a barbed surface engaging a ratchet 272, the ratchet serving to lock the piston rod against translational movement in the proximal direction and/or as a contact for detecting advancement of the piston rod 154 in the distal or proximal direction. In FIG. 23, the piston rod 274 comprises dark and light portions which reflect and absorb light to a different extent, so that an adequate light sensor 276 may provide a signal when the piston rod is advanced in one direction or the other. The ratchet 272 serves to lock the piston rod against translational movement in the proximal direction. In FIG. 24, the engagement of the piston rod 278 and the ratchet 272 causes the ratchet to touch a contact element when the tip of the ratchet 272 passes a peak on the barbed surface of the piston rod 278. Thereby, an electrical pulse is generated each time the piston rod is advanced a distance corresponding to the distance between two successive barbs.

In general, the translational movement of the piston rod 270, 274, 278 during ejection of the drug may be achieved as described in German document DE 68901190, which is hereby incorporated by reference.

Figure 25:
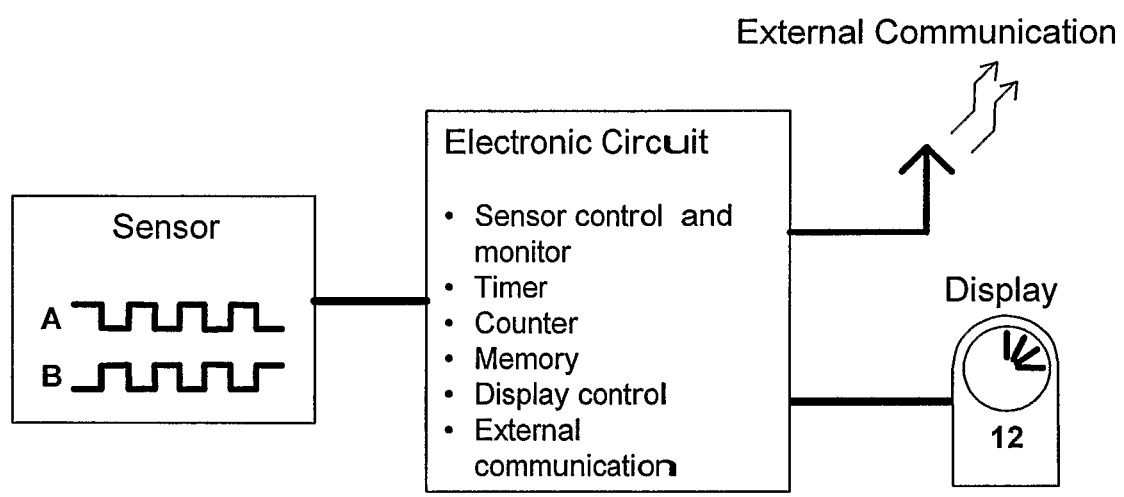
FIG. 25 illustrates a control system of the various embodiments of medication delivery pens.

The control system of any of the sensor arrangements outlined above is diagrammatically illustrated in FIG. 25, in which the sensor itself outputs signals A and B and optionally further signals depending on the number of ratchet arms or other measurement members provided. The signals are passed to an electronic circuit comprising: sensor control and monitor, timer, counter, memory, display control and external communication means. The electronic circuit is arranged to communicate with a display of a medication delivery device and/or with an external device.

The invention claimed is:

1. A medication delivery device comprising:
   a prefilled injection device comprising
      a needle mount that accepts a needle,
      a reservoir having a longitudinal axis and comprising a medicament to be ejected,
      a sensor arranged to detect an ejection of the medicament from the injection device and to subsequently output a signal comprising ejecting information that comprises a dose quantity of the ejected medicament,
      a processor arranged to collect and store the ejection information, and
      a communication structure arranged to transmit the ejecting information to an external data receiving device;
   wherein the reservoir is non-exchangeable, non-refillable, and forms an integral part of the prefilled injection device,
   wherein the sensor comprises a movable part adapted to rotate relative to a stationary part during ejection to determine the ejected dose,
   wherein the moveable part rotates about the longitudinal axis during ejection, and
   wherein the stationary part remains stationary relative to the delivery device during ejection.

2. The medication delivery device according to claim 1, further comprising a cover adapted to cover at least a needle portion of the injection device, wherein the external data receiving device forms an integral part of the cover.

3. The medication delivery device according to claim 2, wherein the cover comprises at least one of:
   a display device arranged to display a representation of the ejecting information; and
   a storage device arranged to store a representation of the ejecting information.

4. The medication delivery device according to claim 2, wherein the cover is attachable to the injection device such that an ejection may only be performed when the cover is removed from the injection device.

5. The medication delivery device according to claim 1, wherein the ejecting information further comprises at least one of:
   time of at least one ejected dose,
   time elapsed since the last ejection,
   an identification of the reservoir,
   an identification of the injection device, and
   an identification of the type of medicament.

6. The medication delivery device according to claim 1, wherein the communication structure comprises one single interface arranged to communicate data to the external data receiving device and to communicate data to a further external data receiving device.

7. The medication delivery device according to claim 1, wherein the communication structure comprises two separate interfaces, one of which is arranged to communicate data to the external data receiving device, and another one of which is arranged to communicate data to a further external data receiving device.

8. The medication delivery device according to claim 1, wherein the communication structure comprises at least one of:
   an electrical conductor,
   a device arranged to transmit wireless data,
   a device arranged to transmit optical data,
   a device arranged to transmit acoustical data,
   a device arranged to transmit capacitive data, and
   a device arranged to transmit inductive data.

9. The medication delivery device according to claim 1, further comprising the external data receiving device on a cover adapted to cover the injection device.

10. A cover for a medication delivery device according to claim 1, comprising:
    a data receiving device and signal receiving structure arranged to receive ejecting information,
    a storage device arranged to store the ejecting information, and
    a display device arranged to display the ejecting information.

11. A kit comprising a medication delivery device according to claim 1 and a cradle structure arranged to perform at least one of:
    supplying electrical power to a data receiving device of a cover adapted to cover the prefilled injection device; and
    transmitting data between the medication delivery device and an external computer.

* * * * *

UNITED STATES PATENT AND TRADEMARK OFFICE
CERTIFICATE OF CORRECTION

| | | |
|---|---|---|
| PATENT NO. | : 10,383,996 B2 | Page 1 of 1 |
| APPLICATION NO. | : 11/665623 | |
| DATED | : August 20, 2019 | |
| INVENTOR(S) | : Miller et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 102 days.

Signed and Sealed this
Fourteenth Day of July, 2020

Andrei Iancu
*Director of the United States Patent and Trademark Office*